(12) United States Patent
Kerins et al.

(10) Patent No.: US 6,638,603 B1
(45) Date of Patent: Oct. 28, 2003

(54) SCREEN PRINTED COATING ON WATER-SENSITIVE FILM FOR WATER PROTECTION

(75) Inventors: John E. Kerins, Neenah; Yihua Chang, Appleton; William S. Pomplun, Neenah, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/912,145

(22) Filed: Aug. 15, 1997

(51) Int. Cl.[7] .................................................. B32B 3/00
(52) U.S. Cl. ........................ 428/195; 428/352; 428/351
(58) Field of Search ................................ 428/352, 353, 428/354, 480, 482, 336, 195, 350, 351; 427/150–152; 503/205, 225, 201, 200; 156/230, 235, 247

(56) References Cited

U.S. PATENT DOCUMENTS

| | | |
|---|---|---|
| 3,550,592 A | 12/1970 | Bernardin |
| 3,554,788 A | 1/1971 | Fechillas |
| 3,559,650 A | 2/1971 | Larson |
| 3,575,173 A | 4/1971 | Loyer |
| 3,636,952 A | 1/1972 | George |
| 3,654,928 A | 4/1972 | Duchane |
| 3,707,430 A | 12/1972 | Costanza et al. |
| 3,881,041 A | 4/1975 | Glienke |
| 4,097,943 A | 7/1978 | O'Connell |
| 4,186,233 A | 1/1980 | Krajewski et al. |
| 4,229,239 A | 10/1980 | Arai et al. |
| 4,269,650 A | 5/1981 | Arai et al. |
| 4,333,464 A | 6/1982 | Nakano |
| 4,372,311 A | 2/1983 | Potts |
| 4,416,791 A | 11/1983 | Haq |
| 4,588,400 A | 5/1986 | Ring et al. |
| 4,654,395 A | 3/1987 | Schulz et al. |
| 4,655,868 A | 4/1987 | Hefele |
| 4,705,584 A | 11/1987 | Lauchenauer |
| 4,731,143 A | 3/1988 | Cross |
| 4,900,554 A | 2/1990 | Yanagibashi et al. |
| 5,009,652 A | 4/1991 | Morgan et al. |
| 5,071,648 A | 12/1991 | Rosenblatt |
| 5,300,358 A | 4/1994 | Evers |
| H1340 H | 7/1994 | Yetter et al. |
| 5,405,475 A | 4/1995 | Kraft et al. |
| 5,468,807 A | 11/1995 | Tsurutani et al. |
| 5,472,518 A | 12/1995 | Patnode et al. |
| 5,509,913 A | 4/1996 | Yeo |
| 5,529,830 A | 6/1996 | Dutta et al. |
| 5,569,348 A | 10/1996 | Hefele |
| 5,584,800 A | 12/1996 | Scholz et al. |
| 5,603,691 A | 2/1997 | Scholz et al. |

FOREIGN PATENT DOCUMENTS

| | | |
|---|---|---|
| EP | 0 461 484 | 12/1991 |
| EP | 479 404 A2 | 4/1992 |
| EP | 0 532 805 | 3/1993 |
| JP | 5-200375 | 8/1993 |
| JP | 5-228172 | 9/1993 |
| JP | 5-293070 | 11/1993 |
| JP | 63-46233 | 12/1994 |
| JP | 7-70525 | 3/1995 |
| WO | WO 94/23769 | 10/1994 |
| WO | WO 96 20831 | 7/1996 |
| WO | WO 97 18082 | 5/1997 |
| WO | WO 99 08727 | 2/1999 |

OTHER PUBLICATIONS

JP 06 100845, Apr. 12, 1994, Abstract.
JP 07 003699, Jan. 6, 1995, Abstract.
JP 06 126901, May 10, 1994, Abstract.
JP 06 134910, May 17, 1994, Abstract.

Primary Examiner—Merrick Dixon
(74) Attorney, Agent, or Firm—Kilpatrick Stockton LLP

(57) ABSTRACT

The present invention is directed to a novel process of making water-sensitive products. In addition, the present invention is directed to water-sensitive products, which maintain their integrity and strength when in use, but dissolve or disperse when place in contact with water, such as in a conventional toilet. Moreover, the present invention is directed to water-dispersible products, including flushable products such as release liners, product packaging, etc., which contain a water-sensitive film strategically coated with a discontinuous hydrophobic material to provide water protection to the film.

22 Claims, No Drawings

SCREEN PRINTED COATING ON WATER-SENSITIVE FILM FOR WATER PROTECTION

FIELD OF THE INVENTION

The present invention is directed to a novel process of making water-dispersible products. In addition, the present invention is directed to water-dispersible products, which maintain their integrity and strength when in use, but dissolve or disperse when placed in contact with water, such as in a conventional toilet. Moreover, the present invention is directed to water-dispersible products, including flushable products such as release liners, product packaging, etc., which possess a tailored degree of water protection due to strategically placed hydrophobic coating material along one or more exterior surfaces of the product.

BACKGROUND OF THE INVENTION

Disposable products have revolutionized modern lifestyle and are of great convenience to society. Such products generally are relatively inexpensive, sanitary and quick and easy to use. Disposal of such products, however, is a concern as landfills close and incineration contributes to urban smog and pollution. Consequently, there is an urgent need for disposable products that can be disposed of without dumping or incineration. An ideal disposal alternative would be the use of municipal sewage treatment and private residential septic systems. Products suited for disposal in sewage systems that can be flushed down a conventional toilet are termed "flushable." An essential feature of flushable products is that they must have sufficient wet strength for their intended use, yet lose structural integrity upon contact with water.

Numerous attempts have been made to produce flushable fibers, fabrics, films and adhesives that retain their integrity and wet strength during use, yet can be disposed of via flushing in conventional toilets. One approach to producing a flushable product is to limit the size of the product so that it will readily pass through plumbing without causing obstructions or blockages. Such products have high wet strength, yet do not disintegrate during flushing. Examples of this type of product include baby wipes. This approach to flushability suffers the disadvantage, however, of being restricted to small sized articles. Many of the current flushable products are limited to such small articles.

Another approach to producing a flushable product is to manufacture a product that is normally insensitive to solutions having a neutral pH such as water, but which disintegrates in the presence of alkaline acidic aqueous solutions. The end user is provided with an alkaline or acidic material to add to the water in which the product is to be disposed. This approach permits disposal via normal plumbing systems of products substantially larger than wipes, but suffers from the disadvantage of forcing the user to perform the step of adding the dissolving chemical to the water. A further disadvantage is that the inadvertent or unintentional disposal of such a product in a conventional toilet without the addition of the dissolving chemical can cause serious obstruction of blockage of the plumbing system. The latter disadvantage can, however, be overcome by incorporating the dissolving acid or alkali into the article, but separate from the dissolvable material while in use. The dissolving chemical is only released upon contact with water during flushing.

Another approach to producing a flushable product is to prepare products such as fibers, fabrics and films from water soluble materials. Upon contact with water, the water soluble material dissolves, reducing the structural integrity of the product, and causing its disintegration, such that it will easily pass through the plumbing system. Although the products prepared by this approach are suitable for applications wherein the product does not come in contact with water, these products are not suited for applications wherein the product may come into contact with even a relatively small amount of water. In applications where a water-sensitive product is most likely to contact water during normal use, the product must possess a degree of water protection. However, too much water protection negatively impairs the flushability of water-sensitive products.

One approach to protecting a water-soluble film from the contact of water is described in U.S. Pat. No. 5,300,358, issued to Evers. Evers discloses degradable absorbent structures comprising a water-impervious backsheet, which rapidly dissolves in cold water. The backsheet comprises a water-soluble polymeric material, usually in the form of a film, coated with a hydrophobic material. The hydrophobic material forms a coating which provides "permanent" water protection, at least until the coating is made discontinuous, for example by tearing the coating with a drawstring, to expose the surface of the water-soluble film. Evers does not disclose or provide guidance regarding the relationship between degree of water protection and coating parameters such as coating pattern, coating thickness, and pore geometry.

What is needed in the art is a method of temporarily protecting a water-sensitive film from water contact so that the film can have optimum utility and yet still readily disperse when placed in a conventional toilet. Also, what is needed in the art is a method of determining optimum coating parameters (i.e., degree of coating, coating thickness, pore geometry, etc.) to maximize the water protection of the film without a continuous or permanent coating. Moreover, a method of producing water resistant, water-sensitive, coated films having tailored degrees of water resistance is also needed.

SUMMARY OF THE INVENTION

The present invention is directed to a novel process of making coated water-sensitive films. Hydrophobic polymers are coated in a discrete pattern of dots on a water-sensitive film using a hot-melt screen printing technique. The coating provides the film with protection from damage by water when the film is brought into contact with water on the coated side. The degree of protection can be controlled by varying the distance between dots. Maximum protection is achieved when the dots touch each other; however, in some applications such as flushable articles, care must be taken to insure that the coating disperses sufficiently so as to not cause clogging during the flushing process of a conventional toilet.

In addition, the present invention is directed to the coated water-sensitive films and articles containing the coated water-sensitive films. Specifically, the coated films of the present invention are useful in connection with a variety of water-dispersible products, and especially absorbent products such as sanitary napkins, diapers, dressings and the like. The articles of the present invention exhibit adequate tensile strength and retain their structural integrity when in contact with body fluids, yet are readily dispersible in water so that the absorbent product may be flushed away after use.

Films are widely used as components of such disposable goods as sanitary napkins, diapers, bandages, and the like.

Such films, if they are to function effectively, must maintain their structural integrity, as well as exhibit satisfactory tensile strength, when they are wet or damp with various body fluids such as blood, menstrual fluid and urine, with which they come into contact during use. It has been recognized that if such films, while retaining their strength in body fluids, were to lose substantially all their tensile strength when exposed to water and become readily dispersible therein, disposal problems would be substantially eliminated since the films could be easily and conveniently disposed of by contacting the film with water. The present invention provides a mechanism for eliminating disposal problems associated with various consumer products.

In a further embodiment of the present invention, the coated film may serve as a primer layer for additional coatings on the water-sensitive film, such as latex coatings. The primer layer provides enough water protection so that a water-base solution coating may be applied to the coated water-sensitive film, the water being subsequently removed prior to any degradation of the water-sensitive film layer. In most cases and applications, the coated water-sensitive film is flushable and dispersible because it will disintegrate rapidly when exposed to water such as in a conventional toilet.

DETAILED DESCRIPTION OF THE INVENTION

The present invention is directed to a novel process of making coated water-sensitive films. Hydrophobic polymer is coated in a discrete pattern of dots on a water-sensitive film, such as a polyethylene oxide (PEO) film, using a hot-melt screen printing technique. The coating provides temporary protection for the film from damage by water when the film is brought in contact with water on the coated side. The degree of protection can be controlled by varying the average distance between dots. Maximum protection is achieved when the dots form a "jigsaw puzzle" pattern, wherein the dots touch each other; however, in some applications such as flushable articles, care must be taken to insure that the coating disperses sufficiently to prevent clogging during the flushing process of a conventional toilet. The screen printing process of the present invention is described below.

Molten hydrophobic polymer is delivered from a melting tank through a heated hose to a slot die located inside a screen cylinder. The temperature of the melting tank, hose and screen cylinder may vary depending upon the melt rheology of the hydrophobic polymer in the coating process. The molten polymer is distributed uniformly on the inner wall of the rotating screen cylinder, and then applied through screen holes, as discrete dots, directly onto the water-sensitive film, or alternatively, onto a carrier substrate outside and adjacent to the screen cylinder. The screen and film/carrier substrate may move at the same or different speeds depending upon the distortion of dot shape desired. When the screen and film/carrier substrate travel at the same speed, symmetrical dots are produced. When the screen and film/carrier substrate travel at different speeds, dots elongated in the machine direction are produced. Elongation of the dots results in bridging of some or all of the dots. Line speed may vary depending upon the "open time" of the hydrophobic polymer. As used herein, the "open time" of a polymer refers to the amount of time required for the polymer to loose its tackiness.

In a transfer coating process, the coated carrier substrate moves further through the process and comes into contact with the water-sensitive film, which is properly aligned with the coated carrier substrate. The coating is transferred from the carrier substrate to the water-sensitive film under pressure as the film and carrier substrate pass through a nip roll. The dots spread out as a result of the nip pressure during the transfer process. The degree of spreading depends on the pressure, open time of the hydrophobic polymer resin, and the coating speed. Desirably, spreading should minimize the gap between dots without coalescence of the dots. In practice, optimum dot spacing is achieved by adjusting processing factors which include, but are not limited to, the hydrophobic polymer, the coating temperature, the screen pattern, the resin flow rate, screen speed, line speed, and the pressure applied at the nip roll.

In either the direct coating process or the transfer coating process, the adhesion of the dots to the water-sensitive film should be greater than the adhesion of the dots to the screen (direct coating) or the carrier substrate (transfer coating). The choice of hydrophobic polymer should take into consideration the desired adhesion properties of the hydrophobic polymer. Suitable hydrophobic polymers for use in the present invention include any processable polymer with appropriate melt rheology and adhesion properties for application by the above-described hot melt screen coating process. Suitable polymers include, but are not limited to, polyolefins, such as polyethylene, polypropylene, and ethylene/propylene copolymers, polyethylene-vinyl acetate, polystyrene, polyesters, polyamides, polyvinyl chloride, fluoropolymers, and silicones.

One or more of the hydrophobic polymers above may be combined to form the coating of the water-sensitive film. Further, the hydrophobic polymer may contain one or more of the following additives including, but not limited to, compatibilizers, processing aids, plasticizers, tacktifiers, detacktifiers, slip agents, and anti-microbial agents, as fabricating agents or as modifiers depending on the specific properties desired in the coating and the final product.

Desirably, the hydrophobic polymer is an amorphous polyolefin having a melt viscosity of about 400 to about 10,000 cps at 190° C. Particularly suitable polymers are manufactured by the U.S. Rexene Company under the tradename REXTAC®. Three REXTAC® resins, RT2315, RT2535 and RT2330, are particularly suitable for the present invention. In a further embodiment, one or more REXTAC® resins are blended with a low molecular weight, highly branched polyolefin to reduce the tackiness of the hydrophobic polymer coating. A particularly suitable low molecular weight, highly branched polyolefin, VYBAR® 253, is manufactured by the Petrolite Corporation. Blends of REXTAC® and VYBAR® 253 provide good results as film coating materials. Desirably, the ratio of REXTAC® resin to VYBAR® 253 is from about 100/0 wt/wt to about 70/30 wt/wt. More desirably, the ratio of REXTAC® resin to VYBAR® 253 is from about 98/2 wt/wt to about 75/25 wt/wt. More desirably, the ratio of REXTAC® resin to VYBAR® 253 is from about 95/5 wt/wt to about 80/20 wt/wt. Particularly useful blends are RT2330/VYBAR® 253 (95/5 wt/wt) and RT2370/VYBAR® 253 (80/20 wt/wt).

The hydrophobic polymer may be coated directly onto the water-sensitive film or onto the carrier substrate and subsequently transferred to the water-sensitive film in the form of a plurality of dots. The dots may have any shape desired. Suitable shapes include, but are not limited to, circles, squares, rectangles, triangles, and hexagons. Desirably, the dot shape allows uniform coverage of the film and minimal spacing between adjacent dots. More desirably, the dots are present as substantially discontinuous interengaged shapes of hydrophobic polymeric material, resembling pieces of a jigsaw puzzle, adhered to and uniformly covering the water-sensitive film surface. As used herein, the phrase "substantially discontinuous" describes a coating wherein the dots are completely distinct from one another with no overlapping of the dots, and also a coating wherein some overlapping of the dots takes place. As used herein, the term "interengaged" describes the relationship of the dots on the film surface such that the exposed surface area of the film is minimized.

Dot size and thickness may vary greatly depending upon the end use of the coated water-sensitive film-containing product. Desirably, dot dimensions should be less than about 100 mm for flushable films to avoid potential clogging in conventional toilets. Dot thickness should be minimized when possible to reduce product cost and to reduce the structural integrity of the coating so that the dots will readily disperse, especially in the case of flushable products. However, the dots should be thick enough to provide a gap between the film surface and the curved air/water interface in the pores between dots. Desirably, the size, thickness and spacing of the dots provide sufficient capillary forces for a given resin coating in order to temporarily provide water protection for the water-sensitive film.

The carrier substrate used in the above-described process may be any substrate which can transfer the hydrophobic polymer to the water-sensitive film. Suitable carrier substrates display little or no adhesion with the hydrophobic polymer relative to the adhesion between the water-sensitive film and the hydrophobic polymer. Suitable carrier substrates include, but are not limited to, release paper, release films, and release-coated substrates such as fabrics and/or belts. Desirably, the carrier substrate is a release paper. More desirably, the carrier substrate is an AKROSIL® High Release Paper.

Water-sensitive films for use in the present invention include any water-sensitive film capable of withstanding the above-described hot melt screen coating process. As used herein, the phrase "water-sensitive film" describes films, which degrade over time when in the present of water and includes, but is not limited to, water-soluble films and water-dispersible films. Suitable water-sensitive films have sufficient strength and adhesion properties for use in the above-described process. Suitable polymers include, but are not limited to, polyalkylene oxides, such as polyethylene oxide (PEO) and polypropylene oxide (PPO), ethylene oxide-propylene oxide copolymers, polymethacrylic acid, polymethacrylic acid copolymers, polyvinyl alcohol, polyethyl oxazoline, polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, polyvinyl methyl oxazolidimone, poly (2-isopropyl-2-oxazoline), and poly (2,4-dimethyl-6-triazinyl ethylene).

The water-sensitive film of the present invention may be made entirely of water-sensitive polymeric material or may contain water-sensitive as well as water-insoluble materials so long as the film dissolves in water, such as in a conventional toilet. Additionally, water-sensitive films may also be made by mixing various different types of water-sensitive film materials. In some embodiments, it may be desirable to employ one or more additives into the water-sensitive film material including, but not limited to, compatibilizers, processing aids, plasticizers, tacktifiers, detacktifiers, slip agents, and anti-microbial agents, as fabricating agents or as modifiers depending on the specific properties desired in the film and the final product.

Desirably the water-sensitive film of the present invention comprises a polyalkylene oxide film or a polyvinyl alcohol film. More desirably, the water-sensitive film of the present invention comprises a polyethylene oxide film, a polypropylene oxide film, an ethylene oxide-propylene oxide copolymer film or a polyvinyl alcohol film. More desirably, the water-sensitive film of the present invention comprises a polyethylene oxide film or a polyvinyl alcohol film. The polyethylene oxide film is the most desirable film for the transfer coating procedure, while the polyvinyl alcohol film is the most desirable film for the direct coating procedure.

The thickness of the water-sensitive film may vary greatly depending upon the end use of the film-containing product. Film thickness should be minimized when possible to reduce product cost and to reduce the time necessary for the film to disperse, especially in the case of flushable products. Desirably, the water-sensitive film thickness will be less than about 2.0 mil. More desirably, the water-sensitive film thickness will be from about 0.1 mil to about 1.4 mil. More desirably, the water-sensitive film thickness will be from about 0.1 mil to about 0.5 mil.

The barrier performance, or degree of water protection, of the coated water-sensitive film depends on a number of factors including, but not limited to, the dot pattern, dot size, the distance between dots, the dot thickness, the pore geometry, the water sensitivity of the film material, and the hydrophobic polymer material. Capillary forces on the surface of the coated film prohibit fluid, such as water, from entering the spaces between dots. The magnitude of capillary forces depends on the factors above and additionally the fluid surface tension, fluid pressure and fluid contact angle on the hydrophobic coating material. Theoretical guidelines for dot spacing may be estimated by reference to the Kelvin equation for a curved air/fluid in a cylindrical pore. The Kelvin equation is given below:

$$\Delta P = P'' - P'$$

$$\Delta P = 2\ \gamma \cos(180 - \theta)/r$$

wherein P″ is the fluid pressure; P′ is the air pressure; ΔP is the capillary pressure difference; γ is the fluid surface tension; θ is the contact angle in degrees; and r is the radius of the pore. If the pressure on the fluid exceeds the sum of the air pressure in the pore and the capillary pressure difference, the fluid will enter into the pore. For example, theoretical calculations for a fluid with a fluid pressure of 0.5 psi, a surface tension of 40 dyne/cm, a non-wetting contact angle of 0° and a cylindrical pore suggests a preferred distance of less than 0.02 mm between the dots in order to keep the fluid out of the pore. In practice, tight spacing of the dots will result in a higher capillary pressure difference and increased temporary water protection.

The degree of water protection of a given coated water-sensitive film may be measured by a water attack test. In the water attack test, a drop of water is placed on the surface of a coated water-sensitive film. The time that it takes for water to wet the water-sensitive film, which is indicated by a change in the appearance of the film, is measured. Desirably, the coated water-sensitive film can withstand a water attack using the above-described test for at least 15 seconds. More desirably, the coated water-sensitive film can withstand a water attack using the above-described test for at least 30 seconds. More desirably, the coated water-sensitive film can withstand a water attack using the above-described test for at least one minute.

With this temporary barrier performance, the screen-printed, coated water-sensitive films of the present invention have applicability in a number of flushable products including, but not limited to, feminine care products, diapers and training pants, bandages, packaging, release films, and the like. Further, the coated water-sensitive films of the present invention are suitable as a primer layer for subsequently applied latex coatings.

Those skilled in the art will readily understand that the coated water-sensitive films of the present invention may be advantageously employed in the preparation of a wide variety of products designed to be contacted with aqueous fluids. Such products may only comprise a single layer of the coated water-sensitive film or may comprise a coated water-sensitive film in combination with one or more additional layers such as coatings, films, fabrics, etc. Although the coated water-sensitive film of the present invention is particularly suited for personal care products, the coated water-sensitive film of the present invention may be advantageously employed in the preparation of a wide variety of consumer products other than personal care products.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Hydrophobic polymer, REXTAC® RT2315, was coated on a high release paper, using a 40 mesh screen, and subsequently transferred to a PEO film under the following conditions: tank temperature, 315° F.; grid temperature, 324° F.; hose temperature, 340° F.; die temperature, 330° F.; screen speed, 35 ft/min.; and line speed, 24 ft/min. Higher line speed facilitated the spreading of dots because of less temperature drop before the nip at pressure. At a line speed of 25 ft/min., coalescence of the dots started to occur. The average space between dots was about 0.1 mm on the release paper and about 0.05 mm on the PEO film. The dot spacing was reduced by increasing the nip pressure.

The effect of mis-matching of the speeds of the screen and the paper was also studied. When the screen was running at higher speed than the paper, flatter dots with less space between them were seen, but coalescence was limited. When the screen speed was slightly less than that of the paper, part of the dot was pulled off as a crescent-shaped wing on one side of the dot, again with little coalescence.

The coated PEO film stood up against droplets of water for 15–30 seconds, and dispersed readily in tap water. Although the coating did not provide long-term protection for the film against water, because of the larger gap between dots, it did protect the film against brief water exposure.

EXAMPLE 2

Hydrophobic polymer, REXTAC® RT2535, was initially coated on a high release paper, using a 40 mesh screen, and subsequently transferred to a PEO film under the following conditions: tank temperature, 330° F.; grid temperature, 340° F.; hose temperature, 345° F.; die temperature, 350° F.; screen speed, 35 ft/min.; and line speed, 24 ft/min. The dots were well separated; the average distance between dots was about 0.25 mm, which provided little protection against water. The nip pressure had a profound effect on dot spreading. When the nip pressure was more than doubled, the average space between the dots was reduced to about 0.1 mm on the PEO film, and more coalescence was observed. The coated PEO film withstood water attack for about 15 seconds and dispersed readily when exposed to a large body of water. Increasing coating temperatures to as much as 375° F. and mismatching the coating speed showed no significant influence on the dot spacing.

EXAMPLE 3

Hydrophobic polymer, REXTAC® RT2330, was coated on a high release paper, using a 40 mesh screen, and subsequently transferred to a PEO film under the following conditions: tank temperature, 336° F.; grid temperature, 345° F.; hose temperature, 344° F.; die temperature 350° F.; screen speed, 35 ft/min.; and line speed, 24 ft/min. Similar to hydrophobic polymer, Rexene RT2315, slight coalescence was observed but not enough for long term protection. Increases in the line speed and nip pressure did not significantly improve the barrier function. The coated PEO film again withstood water attack for 15–30 seconds, and dispersed readily in tap water.

EXAMPLE 4

To increase spreading capacity and to reduce the tackiness of the coating, 5 wt % of a low molecular weight highly branched polyolefin, VYBAR® 253, was added to the RT2330 resin. The blend was coated on a release paper and subsequently transferred to a PEO film under the following conditions: tank temperature, 335° F.; grid temperature, 345° F.; hose temperature, 345° F.; die temperature, 354° F.; screen speed, 35 ft/min.; and line speed, 24 ft/min. The dots were elongated and substantial coalescence occurred. The average space between dots was about 0.2 mm on the release paper and about 0.1 mm on the PEO film. The blend gave the PEO film better water resistance compared to the PEO films coated with RT2315 and RT2330. The film withstood water attack for up to 1 minute, and dispersed readily in tap water.

To further reduce the gap between dots, a 50 mesh screen, which has less space between holes, was used. The dots produced with the 50 mesh screen were smaller and did not coalesce. An increased paper speed of 25 ft/min., while maintaining the screen speed at 35 ft/min., resulted in some pulling of dots, but no improvement in coalescence of dots. An increase in all the temperatures by 10 degrees showed no difference in dot coalescence.

EXAMPLE 5

A blend comprising 80 wt % hydrophobic polymer REXTAC® RT2730 and 20 wt % VYBAR® 253 was coated on a high release paper, using a 40 mesh screen, and subsequently transferred to a PEO film under the following conditions: tank temperature, 301° F.; grid temperature, 303° F.; hose temperature, 309° F.; die temperature, 312° F.; screen speed, 35 ft/min.; and line speed, 25 ft/min. Significantly lower processing temperatures were used because of the relatively large weight percentage of VYBAR® 253. The blend had good spreading capability. The dots appeared flatter, and more coalescence was observed. The average distance between dots was about 0.1 mm. The coated PEO film withstood water attack for over 5 minutes and dispersed readily when exposed to a large body of water.

What is claimed is:

1. A water-sensitive film having temporary protection from water comprising:

a water-sensitive film; and a plurality of substantially discontinuous interengaged shapes of hydrophobic polymeric material on a surface of the water-sensitive film, the shapes having an average spacing between the shapes.

2. The water-sensitive film of claim 1, wherein the average spacing between the shapes is less than 0.2 mm.

3. The water-sensitive film of claim 1, wherein the water-sensitive film is formed by a method comprising the steps of:

providing a hydrophobic polymeric material to a receiving surface of a rotating screen having a screen speed;

contacting a water-sensitive film, having a film line speed, with an applying surface of the rotating screen;

applying a plurality of substantially discontinuous interengaged shapes of the hydrophobic polymeric material onto a surface of the water-sensitive film; and separating the film discontinuously coated with hydrophobic polymeric material from the rotating screen.

4. The water-sensitive film of claim 1, wherein the water-sensitive film is formed by a method comprising the steps of:

providing a hydrophobic polymeric material to a receiving surface of a rotating screen having a screen speed;

contacting a carrier substrate, having a carrier line speed, with an applying surface of the rotating screen;

tranferring a plurality of substantially discontinuous interengaged shapes of hydrophobic polymeric material from the carrier substrate to a water-sensitive film, having a film line speed, by contacting the coated surface of the carrier substrate with the water-sensitive film under pressure; and separating the carrier substrate from the film discontinuously coated with hydrophobic polymeric material.

5. The water-sensitive film of claim 1, wherein the water-sensitive film comprises polyethylene oxide, polypropylene oxide, ethylene oxide-propylene oxide copolyner, polyvinyl alcohol or a combination thereof.

6. The water-sensitive film of claim 1, wherein the hydrophobic polymeric material comprises polyethylene, polypropylene, ethylene/propylene copolymers, polyethylene-vinyl acetate, polystyrene, polyesters, polyamides, polyvinyl chloride, fluoropolymers, silicones or a combination thereof.

7. The water-sensitive film of claim 1, wherein the hydrophobic polymeric material comprises an amorphous polyolefin having a melt viscosity of about 400 to about 10,000 cps at 190° C.

8. The water-sensitive film of claim 1, wherein the water-sensitive film remains substantially unchanged following a water attack for at least 15 seconds.

9. The water-sensitive film of claim 8, wherein the water-sensitive film remains substantially unchanged following a water attack for at least 30 seconds.

10. The water-sensitive film of claim 9, wherein the water-sensitive film remains substantially unchanged following a water attack for at least 60 seconds.

11. A water-sensitive film having temporary protection from water comprising:

a water-sensitive film; and a plurality of substantially discontinuous interengaged shapes of hydrophobic material on a first surface of the water-sensitive film.

12. The water-sensitive film of claim 11, wherein the shapes have an average spacing between the shapes.

13. The water-sensitive film of claim 11, wherein the water-sensitive film comprises polyethylene oxide, polyvinyl alcohol, or a combination thereof.

14. The water-sensitive film of claim 11, wherein the water-sensitive film further comprises a plurality of substantially discontinuous interengaged shapes of hydrophobic material on a second surface of the water-sensitive film, opposite the first surface of the water-sensitive film.

15. The water-sensitive film of claim 11, wherein the watersensitive film has a thickness of less than 2.0 mil.

16. The water-sensitive film of claim 15, wherein the water-sensitive film has a thickness of about 0.1 to about 1.4 mil.

17. The water-sensitive film of claim 16, wherein the water-sensitive film has a thickness of about 0.1 to about 0.5 mil.

18. The water-sensitive film of claim 11, wherein the shapes of hydrophobic material are less than 100 mm in any dimension.

19. A water-sensitive film having temporary protection from water comprising:

a water-sensitive film comprising polyethylene oxide, polypropylene oxide, ethylene oxide-propylene oxide copolymer, polyvinyl alcohol, or a combination thereof; and a plurality of substantially discontinuous interengaged shapes of hydrophobic material on a surface of the water-sensitive film; wherein the hydrophobic material comprises an amorphous polyolefin having a melt viscosity of about 400 to about 10,000 cps at 190° C.

20. The water-sensitive film of claim 19, wherein the shapes have an average spacing between the shapes.

21. The water-sensitive film of claim 20, wherein the average spacing between the shapes is less than 0.2 mm.

22. The water-sensitive film of claim 19, wherein the water-sensitive film remains substantially unchanged following a water attack for at least 15 seconds.

* * * * *